(12) United States Patent
Toutain et al.

(10) Patent No.: US 6,476,043 B1
(45) Date of Patent: Nov. 5, 2002

(54) USE OF CAMPTOTHECIN DERIVATIVES, WITH REDUCED GASTROINTESTINAL TOXICITY

(75) Inventors: Hervé Toutain, Velizy-Villacoublay (FR); Magali Guffroy, Maisons-Alfort (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/762,092

(22) PCT Filed: Aug. 3, 1999

(86) PCT No.: PCT/FR99/01916

§ 371 (c)(1),
(2), (4) Date: Mar. 21, 2001

(87) PCT Pub. No.: WO00/07605

PCT Pub. Date: Feb. 17, 2000

Related U.S. Application Data

(60) Provisional application No. 60/096,318, filed on Aug. 12, 1998.

(30) Foreign Application Priority Data

Aug. 5, 1998 (FR) .............................................. 98 10043

(51) Int. Cl.$^7$ ............................................... A01N 43/42
(52) U.S. Cl. ...................................... 514/280; 514/283
(58) Field of Search .......................... 424/665; 514/280, 514/283

(56) References Cited

U.S. PATENT DOCUMENTS

| | | | | |
|---|---|---|---|---|
| 4,284,579 A | * | 8/1981 | Meischen et al. | 260/429 |
| 4,898,886 A | * | 2/1990 | Larraz | 514/588 |
| 5,225,404 A | | 7/1993 | Giovannella et al. | 514/81 |

FOREIGN PATENT DOCUMENTS

| | | | |
|---|---|---|---|
| JP | 06087746 | * | 3/1994 |
| WO | 9220353 | * | 11/1992 |
| WO | WO 96/11005 | | 4/1996 |

OTHER PUBLICATIONS

Wagener et al, Phase II trial of CPT–11 in patients with advanced pancreatic cancer, an EORTC early clinical trials group study, Annals of Oncology, vol. 6, No. 2, pp. 129–132, 1995.*

Wagener D.J.T., et al., Phase II trial of CPT–11 in patients with advanced pancreatic cancer, an EORTC early clinical trials group study, Annals of Oncology, vol. 6, No. 2, pp. 129–132 (1995).

* cited by examiner

Primary Examiner—Alton Pryor
(74) Attorney, Agent, or Firm—Finnegan, Henderson, Farabow, Garrett & Dunner LLP

(57) ABSTRACT

Use of sodium chloride for preparing an agent intended to reduce or eliminate the gastrointestinal side effects induced by the administration of camptothecin derivatives, characterized in that the sodium chloride solution is administered orally.

13 Claims, No Drawings

USE OF CAMPTOTHECIN DERIVATIVES, WITH REDUCED GASTROINTESTINAL TOXICITY

This application is a 371 of PCT/FR99/01916 filed Aug. 3, 1999 which claims benefit of Ser. No. 60/096,318 filed Aug. 12, 1998.

The present invention relates to the use of camptothecin derivatives, without entailing any gastrointestinal intolerance side effects, or with reduced gastrointestinal side effects. The present invention also relates to the use of sodium chloride solutions to reduce the gastrointestinal side effects entailed by the administration of camptothecin derivatives.

It is known that the administration of camptothecin derivatives causes many side effects. In particular in the gastrointestinal tract, they most commonly cause very serious vomiting and diarrhoea which can lead to interruption of the treatment.

European patent EP 137145 describes camptothecin derivatives of general formula:

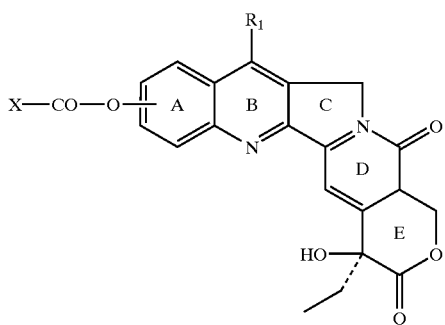

in which, in particular, $R_1$ is hydrogen, halogen or alkyl, X is a chlorine atom or $NR_2R_3$ in which $R_2$ and $R_3$, which may be identical or different, can represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S and/or $NR_4$, $R_4$ being a hydrogen atom or an alkyl radical, and in which the X—CO—O— group is located in positions 9, 10 or 11 on ring A. These camptothecin derivatives are anticancer agents which inhibit topoisomerase I, among which irinotecan, for which X—CO—O— is [4-(1-piperidino)-1-piperidino] carbonyloxy, is an active principle which is particularly effective on solid tumours and especially colorectal cancer.

Patent application EP 74256 also describes other camptothecin derivatives which are also mentioned as anticancer agents, in particular derivatives which have a structure similar to the structure given above and in which X—CO—O— is replaced with a radical —X'R' for which X' is O or S, and R' is a hydrogen atom or an alkyl or acyl radical. Other camptothecin derivatives have also been described, for example, in patents or patent applications P 56692, EP 88642, EP 296612, EP 321122, EP 325247, EP 540099, EP 737686, WO 9003169, WO 9637496, WO 9638146, WO 9638449, WO 9700876, U.S. Pat. No. 7104894, JP 57 116015, JP 57 116074, JP 59 005188, JP 60 019790, JP 01 249777, JP 01246287, JP 91/12070, or in Canc. Res., 38 (1997) Abst. 1526 or 95 (San Diego—12–16 April), Canc. Res., 55(3), 603–609 (1995) or AFMC Int. Med. Chem. Symp. (1997) Abst. PE-55 (Seoul—27 July–1 August).

Camptothecin derivatives are conventionally administered by injection, more particularly intravenously in the form of a sterile solution or of an emulsion. Camptothecin derivatives can also be administered orally, in the form of solid or liquid compositions.

Camptothecin derivatives can also be administered in combination with other anticancer agents, such as for example cisplatin, oxaliplatin, Tomudexo® (N-(5-[N-(3,4-dihydro-2-methyl-4-oxoquinazolin-6-ylmethyl)-N-methylamino]-2-theonyl-L-glutamic acid)), Taxotere® (docetaxel), 5-fluorouracyl and thymidilate synthase inhibitors.

Unfortunately, among the clinical side effects linked to treatment with camptothecin derivatives, the onset of diarrhoea (of grade 3 or 4), of cholinergic syndrome, of nausea or vomiting is especially noted. In particular, in 38% of patients, severe diarrhoea is observed, which can endanger the life of the patients as a result of dehydration and/or associated infection.

Many strategies have been implemented in order to combat intestinal toxicity due to the administration of the active principle and to reduce it, but these have proved unsuccessful hitherto. The result of this is that camptothecin derivatives can only be used by very experienced oncologists and only for certain categories of patients who can tolerate them.

It has now been found, and it is this which forms the subject of the present invention, that protection against the gastrointestinal lesions induced by treatment with camptothecin derivatives can be obtained by the administration of a sodium chloride solution. The protection results in the reduction or even the specific elimination of the gastrointestinal side effects, without the systemic exposure to the active principle or the antitumour activity being reduced.

The present invention relates to the use of sodium chloride for preparing an agent intended to reduce or eliminate the gastrointestinal side effects induced by the administration of camptothecin derivatives. According to the invention, the agent intended to reduce or eliminate the gastrointestinal side effects induced by the administration of camptothecin derivatives is an aqueous sodium chloride solution.

The protection is obtained by administration of a sodium chloride solution simultaneously with the administration of the camptothecin derivative, or alternatively several days before and then simultaneously with the administration of the camptothecin derivative.

This surprising effect has an entirely favourable consequence and, in particular, makes it possible to avoid treatment interruptions linked to the excessively severe gastrointestinal side effects.

According to the invention, the sodium chloride solution used is an aqueous solution which has a concentration of between 4 and 13 g/l. It is administered orally.

Preferably, the sodium chloride solution is used at the concentration of 9 g/l.

The sodium chloride solution is prepared according to conventional methods by dissolving sodium chloride in water (purified water, sterile water, for example). It can also comprise other agents, such as in particular sweeteners or flavourings.

The sodium chloride solution can be administered in a proportion of 5 to 10 ml/kg/administration, once or twice a day, from 5 days before the start of treatment to 1 day after stopping treatment, for a duration of treatment with the camptothecin derivative of between 1 and 5 consecutive days. According to another method of administration, the sodium chloride solution is administered in a proportion of 5 to 10 ml/kg/administration, once or twice a day, for the duration of the treatment, preferably in a proportion of 10 ml/kg/administration, twice a day, for a duration of treatment with the camptothecin derivative of between 1 and 14 consecutive days. Preferably, the sodium chloride solution is used according to this second method of administration.

The camptothecin derivative is administered by injection, preferably intravenous injection, or orally.

When the camptothecin derivative is administered intravenously, these compositions can also contain adjuvants, in particular wetting, isotonicity, emulsifying, dispersing and stabilizing agents. Irinotecan (CPT-11) is in particular administered in solution in a medium for intravenous injection, at doses of between 175 to 500 mg/m$^2$.

The camptothecin derivatives can also be administered orally, in the form of solid compositions such as, for example, hard capsules made of gelatin or of a semi-solid hydrophilic matrix. They can also be administered in the form of tablets, pills, hard capsules, soft capsules, powders or granules. Preferably, the oral compositions can be tablets. In all these compositions, the active product is mixed in particular with one or more inert diluents or adjuvants, such as sugars, sugar derivatives or hydrophilic macromolecules, in particular sucrose, lactose, glucose, maltose, D-fructose, sorbitol, starches such as wheat starch, corn starch or rice starch, cellulose and its derivatives such as ethylcellulose, methylcellulose, hydroxyethylcellulose, hydroxypropylcellulose, methylhydroxymezhylcellulose, methylhydroxypropylcellulose, or carboxymethylcellulose, for example, or gums such as gum arabic, gum tragacanth, guar gum, alginates, carrageenates or dextrin, for example, or proteins, synthetic products such as polyvinylpyrrolidone, high molecular weight PEGs, or alternatively such as inorganic products, for instance colloidal silicas or silicates. These compositions can comprise other substances, such as for example lubricants such as magnesium stearate or a coating intended for controlled release. They can also be administered in the form of pharmaceutically acceptable solutions, suspensions, emulsions, syrups and elixirs containing inert diluents such as water or oils such as liquid paraffin. These compositions can also comprise substances other than diluents, such as wetting, sweetening or flavouring products such as, in particular, sugars or polyols.

It is understood that the presentation kits for the formulation of camptothecin derivatives and of an agent based on sodium chloride, which is intended to reduce or eliminate the gastrointestinal side effects induced by the administration of camptothecin derivatives, also fall within the context of the present invention.

Any form of presentation kits can be suitable, in particular, by way of example, presentations in twin-bottle or multiple-bottle form, presentations in the form of a bottle containing the camptothecin derivative and of one or more vial(s) containing the agent, presentations in the form of an infusion bag containing the camptothecin derivative and of one or more bottle(s) or vial(s) containing the agent, presentations which involve an oral presentation comprising the camptothecin derivative and one or more bottles or vials comprising the agent. It is understood that in the above bottles or vials, the sodium chloride can be in the form of powder to be diluted, or in the form of a solution, in particular a ready-to-use solution.

Experimental Studies:

The present invention has been demonstrated in various studies carried out in mice and dogs, under the conditions described below.

Preparation of an Injectable Solution:

A solution for injection based on irinotecan hydrochloride trihydrate is prepared in a proportion of 20 mg/ml, in the presence of the following constituents:

irinotecan hydrochloride trihydrate . . . 20 mg
D-sorbitol . . . 45 mg
lactic acid . . . 0.9 mg
sodium chloride . . . qs pH=3.5
water for injectable preparations . . . qs 1 ml 1/Experimental Studies in Mice 1.1/Study I Evaluation of the protective effect of an orally administered sodium chloride solution on the intestinal toxicity of intravenously administered CPT-11.

CD1 male mice (5 to 6 weeks old) separated into two groups of 10 receive, in each of the 2 groups, an intravenous injection (20 ml/kg at a rate of 0.5 ml/minute) of an aqueous solution of CPT-11 in sodium chloride at 9 g/l, at the dose of 40 mg/kg (approximately 120 mg/m$^2$ of body surface), for 5 consecutive days from day 6 to day 10. This period of treatment is followed by a period of 3 days without treatment (up to day 13). In one of the groups, the mice also receive, orally, an aqueous sodium chloride solution at 9 g/l at a volume of 20 ml/kg/day (i.e. 10 ml/kg/administration, twice a day approximately 10 hours apart) for 10 consecutive days (days 1 to 10) (CPT-11/NaCl group). The animals in the second group do not receive 9 g/l sodium chloride orally (CPT-11 group).

The mortality and the clinical symptoms are observed every day. The body weight is recorded on days 1, 6, 11 and 13. The mice are sacrificed and autopsied on day 13. The complete gastrointestinal tract is removed from all of the mice. The gastrointestinal tract of the mice which survived to the end of the observation period is subjected to examination under a microscope.

The mortality linked to the administration of CPT-11 observed on days 6 and 7 is observed in 7/15 mice in the CPT-11 group and in only 2/10 mice in the CPT-11/NaCl group. Reductions in motor activity, trembling, convulsions and/or respiratory difficulties linked to the administration of CPT-11 are occasionally observed after the administration of CPT-11. Loss of body weight is observed in the CPT-11 and CPT-11/NaCl groups throughout the treatment with CPT-11. The loss of body weight is greater in the CPT-11 group than in the CPT-11/NaCl group and persists after the end of the treatment in the CPT-11 group.

The nature of the microscopic lesions observed in the intestine corresponds to those expected with an anticancer agent. The lesions are mainly in the small intestine for the two groups. These lesions, which are moderate to pronounced overall, are characterized by a loss of crypts and shortening of the villi. The intestinal lesions are less severe in the CPT-11/NaCl group, in particular, minimal losses this crypts are observed only occasionally.

In conclusion, the oral administration of an isotonic sodium chloride solution (9 g/l) at 10 ml/kg/administration twice a day (20 ml/kg/day) for 5 days before, and during, the intravenous administration of CPT-11 for 5 days prevents the occurrence of the intestinal histopathological lesions induced by CPT-11.

1.2/Study II

Evaluation of the protective effect of various protocols of oral administration of a sodium chloride solution on the intestinal toxicity of CPT-11.

CD1 male mice (5 or 6 weeks old) are divided into 5 groups of 10 animals and receive an intravenous injection (20 ml/kg at a rate of 0.5 ml/minute) of an aqueous solution of CPT-11 in sodium chloride at 9 g/l, at the dose of 40 mg/kg (approximately 120 mg/m$^2$ of body surface), for 5 consecutive days from day 6 to day 10. A sodium chloride solution of 9 g/l is administered twice a day in a proportion of 10 ml/kg/administration (approximately 10 hours apart) from day 1 to day 10 for group 1, twice a day in a proportion of 5 ml/kg/administration from day 1 to day 10 for group 2, once a day in a proportion of 20 ml/kg/administration from day 1 to day 10 for group 3, and twice a day in a proportion of 10 ml/kg/administration from day 6 to day 10 for group 4. The animals in group 5 receive no 9 g/l sodium chloride solution.

The mortality and the clinical symptoms are observed every day. The body weight is measured on days 3, 6, 10 and 13. The mice are sacrificed and autopsied on day 13. The complete gastrointestinal tract is removed from all the mice. The gastrointestinal tract of the mice which survived to the end of the observation period is subjected to examination under a microscope.

The clinical symptoms observed in all of the groups are similar to those recorded in the above study (study I). A reduction in body weight is observed in all the groups.

The microscopic lesions observed in the intestine correspond to those expected with an anticancer agent. The lesions are mainly in the small intestine in all the groups. The intestinal lesions are less severe in the groups which received 9 g/l sodium chloride solution orally than in the group treated with CPT-11 alone. On the other hand, the incidence and severity of the intestinal lesions are identical in groups 1 to 4 which received, orally, a 9 g/l sodium chloride solution using a different administration protocol.

In conclusion, the oral administration of an isotonic sodium chloride solution (9 g/l) once or twice a day at various administration volumes (5 to 20 ml/kg/administration) before and during, or only during, the intravenous administration of CPT-11 for 5 days prevents in a comparable manner the occurrence of the intestinal histopathological lesions induced by CPT-11.

1.3/Study III

Evaluation of the effect of an orally administered isotonic sodium chloride solution on the intestinal and systemic toxicity of CPT-11 and on the toxicokinetics of CPT-11 and of its principal metabolite, SN-38.

CD1 male mice (5 to 6 weeks old) are separated into 3 groups of 10. The animals of 2 groups receive an intravenous injection (20 ml/kg at a rate of 0.5 ml/minute) of an aqueous solution of CPT-11 in sodium chloride at 9 g/l, at the dose of 40 mg/kg (approximately 120 mg/m$^2$ of body surface), for 5 consecutive days from day 1 to day 5. This period of treatment is followed by a period of 3 days without treatment (up to day 8). In one of these two groups, the mice also receive, orally, an aqueous sodium chloride solution at 9 g/l at a volume of 20 ml/kg/day (i.e. 10 ml/kg/administration, twice a day approximately 10 hours apart) for 5 consecutive days (days 1 to 5) (CPT-11/NaCl group). The animals in the second group receive no 9 g/l sodium chloride orally (CPT-11 group). In the third group, which did not receive CPT-11, the mice receive, orally, an aqueous sodium chloride solution at 9 g/l at a volume of 20 ml/kg/day (i.e. 10 ml/kg/administration, twice a day approximately 10 hours apart) for 5 consecutive days (days 1 to 5) (control group). An additional 36 animals in the CPT-11 and CPT-11/NaCl groups are used to determine the plasmatic concentrations of CPT-11 and its principal metabolite, SN-38.

The mortality and the clinical symptoms are observed every day. The body weight is measured on days 1, 3, 6 and 8. The plasma samples for the toxicokinetic analysis are taken on days 1 and 5. The mice are sacrificed and autopsied on day 8. The relative and absolute weights of the thymus, of the spleen and of the testicles are measured, and the complete gastrointestinal tract, the sternal bone marrow, the thymus, the spleen, the testicles and the epididymes are removed from all the mice and subjected to examination under a microscope.

The maximum plasma concentrations (Cmax) and the areas under the curve (AUC) measured for CPT-11 and SN-38, its principal metabolite, are identical for the animals in the CPT-11 and CPT-11/NaCl groups on days 1 and 5.

The mortality linked to the administration of CPT-11 observed on day 8 is observed in 1/10 animals in the CPT-11/NaCl group. The reductions in motor activity and respiratory difficulties linked to the administration of CPT-11 are observed occasionally after administration of CPT-11 in the CPT-11 and CPT-11/NaCl groups, with greater severity in the CPT-11/NaCl group. Identical losses of body weight are observed in the CPT-11 and CPT-11/NaCl groups throughout the treatment with CPT-11, and continue after the end of the treatment.

The microscopic lesions observed in the thymus and intestine correspond to those expected with an anticancer agent. The microscopic lesions observed in the thymus of the animals in the CPT-11 and CPT-11/NaCl groups are similar and are characterized by lymphoid depletion associated with a reduction in the weight and size of this organ. The intestinal microscopic lesions are mainly in the small intestine for the CPT-11 and CPT-11/NaCl groups and are characterized mainly by a loss of crypts and atrophy of the villi. The intestinal lesions are less severe in the CPT-11/NaCl group than in the CPT-11 group.

In conclusion, the oral administration of an isotonic 9 g/l sodium chloride solution twice a day at 10 ml/kg/administration (20 ml/kg/day) during the intravenous administration of CPT-11 for 5 days does not modify the systemic exposure to CPT-11 and to SN-38, does not alter the thymic toxicity of CPT-11, but selectively reduces the severity of the intestinal lesions induced by CPT-11.

1.4/Study IV

Evaluation of the effect of the oral administration of a sodium chloride solution on the antitumour activity of intravenously administered CPT-11.

C3H/HeN female mice carrying a mammary adenocarcinoma MA16/C implanted subcutaneously on day 1 are separated into two groups and receive, in each of the 2 groups, an intravenous injection (20 ml/kg) of an aqueous solution of CPT-11 in 5% glucose, at a dose of 14.6, 23.6, 38.0 or 61.3 mg/kg, for 5 consecutive days from day 6 to day 10. In one group, the mice also received, orally, an aqueous sodium chloride solution at 9 g/l at a volume of 20 ml/kg/day (i.e. 10 ml/kg/administration, twice a day approximately 10 hours apart) for 10 consecutive days (days 1 to 10) (group CPT-11/NaCl). The animals in the second group receive no 9 g/l sodium chloride orally (CPT-11 group).

The antitumour activity of CPT-11 is evaluated at the maximum nontoxic dose. A dose which produces a loss of body weight of more than 20%, or an incidence of mortality linked to the administration of CPT-11 of more than 20%, is considered to be too toxic. The parameters evaluated include the inhibition of tumour growth (T/G) expressed as a percentage, the delay in tumour growth (T-G) and the number of tumour cells killed (Log tumor cell kill=T-G/3.32×tumour doubling time). A Log tumour cell kill value of 0.7 corresponds to minimum activity, while a value greater than 2.8 corresponds to a high level of activity.

For the animals in the CPT-11 group, the maximum nontoxic dose of CPT-11 is 23.6 mg/kg/day, i.e. a total cumulative dose of 118 mg/kg, the maximum loss of body weight is 10% on day 11 and the Log cell kill value is 1.7. For the animals of the CPT-11/NaCl group, the maximum nontoxic dose of CPT-11 is 38.0 mg/kg/day, i.e. a total cumulative dose of 190 mg/kg, the maximum loss of body weight is 14.1% on day 12 and the Log cell kill value is 2.3.

In conclusion, the oral administration of an isotonic sodium chloride solution (9 g/l) at 10 ml/kg/administration twice a day (20 ml/kg/day) for 5 days before, and during, the intravenous administration of CPT-11 for 5 days does not reduce the antitumour activity of CPT-11.

2/Experimental Study in Dogs

Evaluation of the protective effect of an orally administered sodium chloride solution on the intestinal toxicity of CPT-11 by the intravenous route.

Six female Beagle dogs (10 to 12 months old) are separated into two groups of 3 and receive, in each of the 2 groups, a single intravenous injection (5 ml/kg at a rate of 2 ml/minute) of an aqueous solution of CPT-11 in sodium chloride at 9 g/l, at a dose of 20 mg/kg (approximately 400 mg/M$^2$ of body surface), on day 6. In one group, the animals also receive, orally, an aqueous sodium chloride solution. at 9 g/l at a volume of 20 ml/kg/day (i.e. 10 ml/kg/administration, twice a day approximately 8 hours apart) for 7 consecutive days (days 1 to 7) (CPT-11/NaCl group) from 5 days before to 1 day after the administration of CPT-11. The animals in the second group receive no 9 g/l sodium chloride orally (CPT-11 group). The animals are kept with no administration for 2 days after the final administration of sodium chloride at 9 g/l (up to day 9).

The mortality and the clinical symptoms are observed every day. The body weight is recorded during the pretest period and on days 5 and 9. The animals are sacrificed and autopsied on day 9. Representative tissue samples taken from the gastrointestinal tract are removed from all the animals and subjected to examination under a microscope.

The effects linked to the administration of CPT-11 during the period of treatment comprise salivation, restlessness, vomiting (during or immediately after the administration of CPT-11), diarrhoea and a slight loss of weight. Observation of the large intestine reveals redness on the mucosa which is more common in the CPT-11 group than in the CPT-11/NaCl group. The lesions observed result from primary modification of the proliferative compartment and consist of degeneration of the mucosa, and are moderate to pronounced in the CPT-11 group and minimal to mild in the CPT-11/NaCl group.

In conclusion, the intravenous administration of a single dose of CPT-11 to female dogs, at the dose of 20 mg/kg, produces gastrointestinal toxicity compatible with the antimitotic activity of the product. The oral administration of an isotonic sodium chloride solution (9 g/l) at 10 ml/kg/administration twice a day (20 ml/kg/day) from 5 days before to 1 day [lacuna] the administration of CPT-11 prevents the occurrence of the histopathological lesions induced by CPT-11.

What is claimed is:

1. A medicinal product comprising:

a) a first solution comprising one or more camptothecin derivatives, wherein the derivative is of the formula:

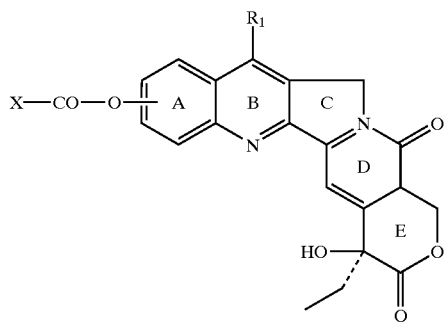

and wherein

R$_1$ is a hydrogen, halogen, or alkyl,

X is a chloride atom or NR$_2$R$_3$, wherein R$_2$ and R$_3$, which may be identical or different, can represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S, and/or NR$_4$, R$_4$ being a hydrogen atom or an alkyl radical, and in which the X—CO—O— group is located in positions 9, 10, or 11 on ring A, and b) a second solution consisting essentially of sodium chloride, which is administered orally during, or before and during, the administration of the first solution.

2. The medicinal product of claim 1, wherein sodium chloride concentration is between 4 and 13 g/l.

3. The medicinal product of claim 2, wherein the sodium chloride concentration is 9 g/l.

4. The medicinal product of claim 1, wherein the camptothecin derivative is irinotecan (CPT-11).

5. A medicinal product comprising:

a) a first solution comprising one or more camptothecin derivatives, wherein the derivative is of the formula:

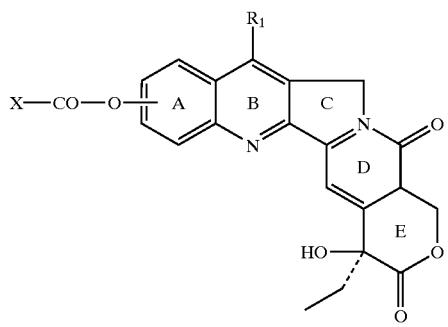

and wherein

R$_1$ is a hydrogen, halogen, or alkyl,

X is a chloride atom or NR$_2$R$_3$, wherein R$_2$ and R$_3$, which may be identical or different, can represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S, and/or NR$_4$, R$_4$ being a hydrogen atom or an alkyl radical, and in which the X—CO—O— group is located in positions 9, 10, or 11 on ring A, and b) sodium chloride which is administered orally during, or before and during, the administration of the first solution, further comprising one or more anticancer agents selected from the group consisting of cisplatin, oxaliplatin, N-(5-[N-(3,4-dihydro-2-methyl-4-oxoquinazolin-6-ylmethyl)-N-methylamino]-2-theonyl-L-glutamic acid)), docetaxel, 5-fluorouracyl and thymidilate synthase inhibitors.

6. A method of treating a cancer by administering to a patient an effective amount of a medicinal product comprising:

a) a first solution comprising one or more camptothecin derivatives, wherein the derivative is of the formula:

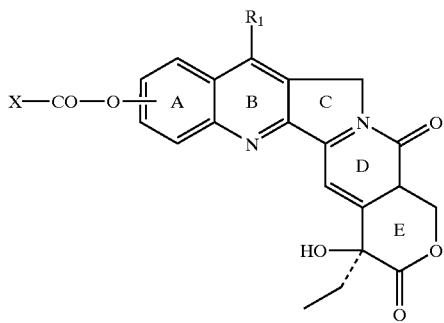

and wherein $R_1$ is a hydrogen, halogen, or alkyl,

X is a chloride atom or $NR_2R_3$, wherein $R_2$ and $R_3$, which may be identical or different, can represent a hydrogen atom, an optionally substituted alkyl radical, a carbocycle or a heterocycle which are optionally substituted, or alkyl radicals (optionally substituted) forming, with the nitrogen atom to which they are attached, a heterocycle optionally containing another hetero atom chosen from O, S, and/or $NR_4$, $R_4$ being a hydrogen atom or an alkyl radical, and in which the X—CO—O— group is located in positions 9, 10, or 11 on ring A;

b) a second solution consisting essentially of a sodium chloride solution, wherein the second solution is administered orally during, or before and during, the administration of the first solution, and c) wherein the second solution eliminates or reduces the gastrointestinal side effects associated with the administration of camptothecin derivatives alone.

7. The method of claim 6, wherein the camptothecin derivative is irinotecan (CPT-11).

8. The method of claim 7, wherein the irinotecan is administered in a solution at doses between 175 and 500 mg/m$^2$ of body surface.

9. The method of claim 6, wherein the sodium chloride is administered orally in a proportion of 5 to 10 ml/kg/administration.

10. The method of claim 6, wherein the first solution of the medicinal product is administered by injection or orally.

11. The method of claim 6 or 7, wherein the cancer is a cancer of the gastrointestinal tract.

12. The method of claim 6 or 7, wherein the cancer is colorectal cancer.

13. A kit comprising the medicinal product of claim 1 or 4, wherein the first and the second solution are intended for separate administration.

* * * * *